US00PP16622P3

(12) United States Plant Patent
Janick et al.

(10) Patent No.: US PP16,622 P3
(45) Date of Patent: Jun. 6, 2006

(54) APPLE TREE NAMED 'CO-OP 39'

(50) Latin Name: *Malus domestica*
Varietal Denomination: CO-OP 39

(75) Inventors: Jules Janick, West Lafayette, IN (US); Edwin B. Williams, Lafayette, IN (US); Joseph C. Goffreda, Millstone Township, NJ (US); Schuyler S. Korban, Champaign, IL (US)

(73) Assignee: Purdue Research Foundation, West Lafayette, IN (US)

( * ) Notice: Subject to any disclaimer, the term of this patent is extended or adjusted under 35 U.S.C. 154(b) by 102 days.

(21) Appl. No.: 10/971,713

(22) Filed: Oct. 22, 2004

(65) Prior Publication Data

US 2006/0090229 P1 Apr. 27, 2006

(51) Int. Cl.
*A01H 5/00* (2006.01)

(52) U.S. Cl. ..... Plt./161

(58) Field of Classification Search ..... Plt./161
See application file for complete search history.

*Primary Examiner*—Kent Bell
*Assistant Examiner*—W. C. Haas
(74) *Attorney, Agent, or Firm*—Klarquist Sparkman

(57) ABSTRACT

A new apple variety distinguished by resistance to apple scab; crisp flesh and excellent dessert quality; attractive color (almost completely red); ripens in the middle of September in West Lafayette, Ind.; size varies from 2.75 to 3 inches in diameter; and good storage ability (can be stored up to six months at 1° C.).

2 Drawing Sheets

Latin name of the genus and species of the plant claimed: *Malus domestica.*
Variety denomination: 'CO-OP 39'.

CROSS REFERENCE TO RELATED APPLICATIONS

None.

STATEMENT REGARDING FEDERALLY SPONSORED RESEARCH OR DEVELOPMENT

None.

BACKGROUND OF THE INVENTION

The present invention relates to a new and distinct variety of apple tree named 'CO-OP 39'. Our new tree resulted from a planned hybridization program and is a selection from crossing 'PCFW2-134' (unpatented) as the seed parent with 'PR1 669-205', an unpatented apple tree, as the pollen parent (see FIG. 1). The original cross was performed in 1971 in New Jersey. The resulting tree was selected when growing in a cultivated area in West Lafayette, Ind.

BRIEF SUMMARY OF THE INVENTION

The 'CO-OP 39' variety is distinguished from other apple varieties due to the following unique combination of characteristics: resistance to apple scab; very crisp flesh and excellent dessert quality; very attractive color (almost completely red); ripens in the middle of September in West Lafayette, Ind.; size varies from 2.75 to 3 inches in diameter; and good storage ability (can be stored up to six months at 1° C.).

Asexual reproduction of this new variety by grafting and budding onto rootstock ['Malling 7' (unpatented) rootstocks] shows that the foregoing characteristics come true to form, are firmly fixed, and are established and transmitted through succeeding propagations.

The following detailed description concerns the original tree, selected on Sep. 18, 1979, and progeny first asexually propagated in 1980. The original tree and progeny have been observed growing in a cultivated area in West Lafayette, Ind.

Certain characteristics of this variety may change with changing environmental conditions (such as photoperiod, temperature, moisture, soil conditions, nutrient availability, or other factors). For example, leaf colors may be brighter green if the trees are grown in soil with greater nitrogen concentrations, and may be more yellow when grown in soil containing lesser amounts of nitrogen. Color descriptions and other terminology are used in accordance with their ordinary dictionary descriptions, unless the context clearly indicates otherwise. Color designations (hue/value/chroma) are made with reference to The Royal Horticultural Society Colour Chart (R.H.S.).

Figure 1:
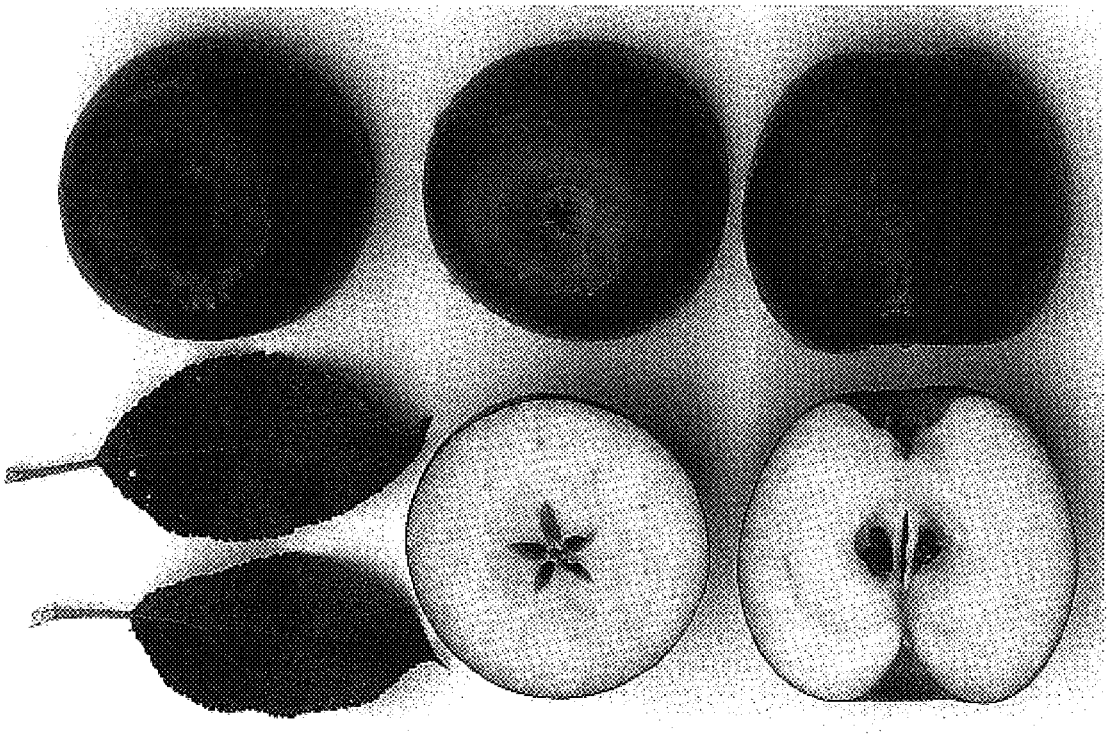
FIG. 1 is a photograph showing typical fruit and leaves of the new variety.
Figure 2:
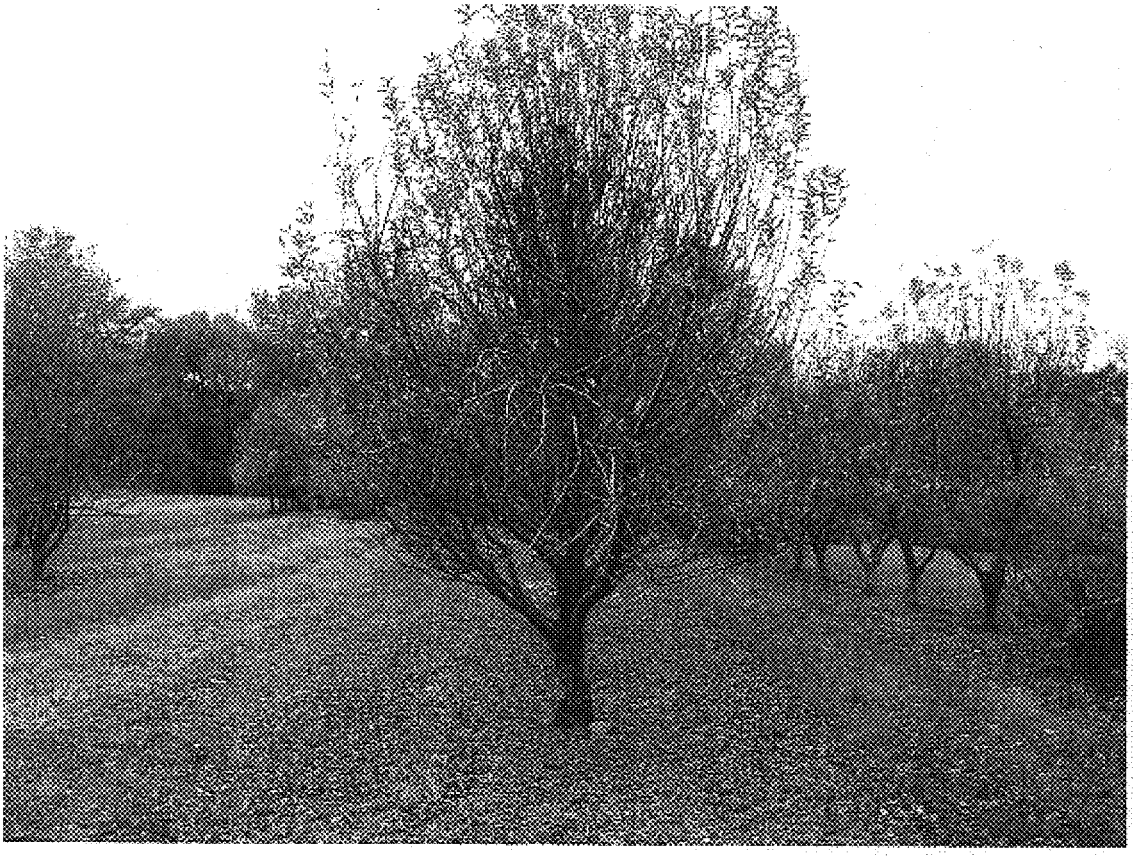
FIG. 2 is a photograph showing a tree of the new variety.

The accompanying color photographs shows typical specimens of the leaves and fruit and tree of this new apple tree variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photographs alone.

DETAILED DESCRIPTION

BOTANICAL

The following detailed description of the 'CO-OP 39' (Crimson Crisp) variety is based on observations of asexually reproduced progeny. The observed progeny are trees which were 24 years of age and growing on 'Malling 7' rootstock in West Lafayette, Ind.

Scientific name: *Malus domestica* 'CO-OP 39'.

Parentage:

*Seed parent.*—PCFW2-134.

*Pollen parent.*—PR1 669-205.

Tree:

*Vigor.*—Low.

*Overall shape.*—Round.

*Height.*—About 15 feet to 17 feet.

*Width.*—Overall spread of about 16 feet.

*Caliper.*—8 inches at 12 inches above the ground.

*Trunk.*—Stocky.

*Trunk bark texture.*—Rough and scaly.

*Trunk bark color.*—Greyed-green (RHS 191A).

*Patches or other markings.*—Exfoliates, greyed-orange (RHS N167C-D).

*Primary branches.*—Upright. Angle of emergence from trunk: about 40 degrees to about 45 degrees. Angle does not vary from top to bottom of tree.

*Branch color.*—One-year old branches are greyed-purple (RHS N186A) in color, while two-year old branches are brown (RHS N200B) in color.

*Branch pubescence.*—New wood: Yes, yellow green (RHS 147D). Older wood: No.

*Branch lenticels.*—Medium density, approximately 14 per square centimeter; elongated, typical examples of which measured about 1 mm in diameter; white (RHS N155B) in color.

*Internodes.*—Average internode length is about 2.5 cm on a one-year old shoot.

*Bearing.*—Annual.

*Hardiness.*—Zones 5B.

*Disease resistance.*—Field immune to apple scab, but susceptible to Cedar Apple Rust and fireblight.

Leaves:

*Texture.*—Medium.

*Sheen.*—Dull.

*Length.*—About 70.9 mm to about 89.5 mm, averaging about 82.8 mm in 10 leaves.

*Width.*—About 38.7 mm to about 64.2 mm, averaging about 51.6 mm in 10 leaves.

*Thickness.*—About 0.2 mm to about 0.5 mm, averaging about 0.3 mm in 10 leaves.

*Petiole.*—About 23.1 mm long; yellow green in color (RHS 147D); about 1.7 mm in diameter. Fine pubescence. Base of petiole in grey-purple in color (RHS 184D).

*Margin.*—Serrate.

*Tip shape.*—Acuminate.

*Stipules.*—2 stipules in opposite arrangement; yellow green (RHS 147D) in color; about 0.1 mm wide.

*Leaf color.*—Upper leaf surface: Yellow-green (RHS 146A). Lower leaf surface: Yellow-green (RHS 147D). Vein: Yellow-green (RHS 147D).

*Pubescence.*—None.

The length, width, thickness and other measurements were obtained from observations of ten typical leaves in West Lafayette, Ind. on Sep. 14, 2004.

Flowers:

*Size.*—Medium size, typical flower measuring about 46.0 mm across.

*Shape.*—Radially symmetrical.

*Color.*—Unopened bud: Red-purple (RHS 67A). Opened flower: Red-purple (RHS 65C) to white (RHS N155D).

*Petals.*—5 petals per flower; about 23 mm (to slightly larger) inch long. Red-purple (RHS 65C) to white (RHS N155D) in color.

*Stamen.*—Arranged in a single row. 20 stamens, each about 10 mm long and red-purple (RHS 69D) in color.

*Anthers.*—Yellow (RHS 2A) in color.

*Pistil.*—Stigma is about 10 mm long; 5 styles, fused at base, and green-yellow (RHS 1B) in color.

*Sepals.*—About 8 mm and about 4 mm wide (at base); recurved shape; yellow-green (RHS 144B) in color; purple in color at tip; pubescent.

*Pollen.*—Yellow (RHS 2C) in color.

*Fragrance.*—Slight.

*Bloom season.*—In 2004 in West Lafayette, Ind., full bloom observed on May 1 for 'CO-OP 39', April 27 for the 'Delicious' (unpatented) variety; April 30 for the 'Golden Delicious' (unpatented) variety.

Fruit: (Observations from a limited number of typical fruit in West Lafayette, Ind.).

*Size.*—Medium; size varies from 2.75 to 3 inches in diameter.

*Form.*—Oblate to round; symmetric. Length to diameter ratio 0.92; no ribbing; no lobes at calyx end.

*Cavity.*—Medium acute; about 12.1 mm deep and about 30.4 mm wide.

*Basin.*—Wide; about 6.8 mm deep and about 27.7 mm wide; no pubescence observed.

*Stem.*—Short; about 11.8 mm long and 3.5 mm in diameter; greyed-orange (RHS 177B) in color.

*Locules.*—Small; 5 locules; closed. Seeds adhere to carpel wall.

*Skin.*—Medium with glossy finish. No tendency to become waxy or oily in storage.

*Lenticels.*—Inconspicuous; red-purple (RHS 61D); round.

*Color.*—General color effect: Overcolor is red-purple (ranging from RHS 60A–60D) in color with dark purple blush (RHS 60A) coloring. Ground color: Red-purple (RHS 60C). Overcolor: Blush is a dark purple (RHS 59A). Undercolor at calyx end is green yellow (RHS 1B). Russet: none.

*Fruit properties at picking on Sep. 10, 2004 in West Lafayette, Ind.*—Acid content: About 0.633 g/100 ml malic acid. Firmness: About 7 kg, averaging about 10 kg. Soluble solids: About 13.5% to 16.5%. Starch index: On a scale of 1 (high starch) to 8 (low starch), average about 6.2. Flavor: Rich and complex. Juiciness: Moderately juicy. Flesh color: Yellow (RHS 4D). Aroma: Slight.

*Core.*—Median bundle area shape; about 27.42 mm long and about 22.3 mm wide; calyx tube closed with a length of about 5.3 mm. Core lines defined weakly.

*Seed.*—About 2 seeds per cell; acute shaped; about 10.9 mm long and about 4.4 mm wide; greyed-red (RHS 178B) in color.

*Fruit production.*—First picking date in 2004 in West Lafayette, Ind. was about September 15, and last picking date was about October 10.

*Storage.*—Fruit remains fresh at room temperature for many days, and can be stored up to 4 months in cold storage (1° C.).

*Usage.*—Dessert.

We claim:

1. A new and distinct variety of apple tree, substantially as herein shown and described.

* * * * *